United States Patent [19]

Harris

[11] Patent Number: 5,270,051
[45] Date of Patent: Dec. 14, 1993

[54] ENZYME-ORTHOKERATOLOGY

[76] Inventor: Donald H. Harris, 32494 Adriatic, Laguna Niguel, Calif. 92677

[21] Appl. No.: 776,211

[22] Filed: Oct. 15, 1991

[51] Int. Cl.⁵ .............. A61F 2/14; A61K 37/54; C12N 9/26; C12N 11/08
[52] U.S. Cl. .............. 424/427; 424/94.62; 424/423; 424/428; 424/429
[58] Field of Search .............. 424/94.62, 427, 428, 424/429, 423, 78.04; 514/912; 435/180, 182, 201; 623/4, 5

[56] References Cited

U.S. PATENT DOCUMENTS

| | | | |
|---|---|---|---|
| 1,929,228 | 10/1933 | Wilhelm | 351/160 R |
| 3,302,646 | 2/1967 | Behney | 424/429 |
| 3,416,530 | 12/1968 | Ness | 424/427 |
| 3,485,244 | 12/1969 | Rosen | 424/429 |
| 3,710,796 | 1/1973 | Neefe | 424/429 |
| 3,760,807 | 9/1973 | Neefe | 424/429 |
| 3,776,230 | 12/1973 | Neefe | 604/291 |
| 3,786,812 | 1/1974 | Neefe | 424/429 |
| 3,831,604 | 8/1974 | Neefe | 424/429 |
| 3,957,049 | 5/1976 | Neefe | 424/429 |
| 4,484,922 | 11/1984 | Rosenwald | 424/429 |
| 4,540,417 | 9/1985 | Poler | 424/429 |
| 4,571,039 | 2/1986 | Poler | 424/429 |
| 4,592,752 | 6/1986 | Neefe | 424/429 |

OTHER PUBLICATIONS

Wyeth Laboratories Inc. Wyeth ® Wydase ® (Hyaluronidase); May 14, 1987.
Chiron Ophthalmics Medilens TM Corneal Shield; Jun. 1990.
Charles Harrison May, OD, FAAO, FIOS Basic Orthokeratology Computerized ®; 1990.
Chiron Ophthalmics Medilens TM Monograph; Undated.
Physician's Desk Reference Product Information Wydase ® (Hyaluronidase) Injection; Undated pp. 2214–2215.
Donald Hughes Harris, Corneal Changes in Myopia Reduction Orthokeratology vol. IV 1978.
Donald Hughes Harris, Accommodate Convergence Control in Myopia Reduction; American Optometric Association Journal vol. 45, No. 3, Mar. 1974.
Donald Hughes Harris, Research Results of 160 Eye Study; National Eye Research Foundation Oct. 1990.
Donald Hughes Harris, Orthokeratology Myopia Control; Newport Beach Optometric Eyecare Center.
Treister, et al., Effect of Hyaluronidase; Arch. Opthal., vol. 81, May 1969, pp. 647–649.

Primary Examiner—Thurman K. Page
Assistant Examiner—C. Azpuru
Attorney, Agent, or Firm—Knobbe, Martens, Olson & Bear

[57] ABSTRACT

Method and refractive errors of the eye are disclosed. Accelerated reshaping of the corneal tissue is accomplished by releasing enzyme(s) and/or other agents into the cornea which temporarily soften the cornea. The convex cornea is thereafter fitted with a rigid contact lens(es) which has a concave curvature that will correct the refractive error. The softened cornea then rapidly reshapes its convex curvature to the concave curvature of the contact lens rendering the eye emmetropic. The enzyme/agent then dissipates from the cornea as it "hardens" to retain the new emmetropic shape and the lens is removed.

12 Claims, 7 Drawing Sheets

ENZYME-ORTHOKERATOLOGY

BACKGROUND OF THE INVENTION enzyme(s) or other agents which facilitate reshaping of the cornea to reduce or eliminate refractive errors of the eye.

Approximately eighty percent of the refracting power of the eye is at the cornea. When the cornea is misshapen or the axial length of the eye is too long or short, or the lens of the eye is functioning abnormally, the refractive errors of myopia, astigmatism or hyperopia can result. Spectacles correct refractive errors by refracting the light with a lens before it reaches the cornea in order to change the angle at which light enters the cornea. Contact lenses correct refractive errors of the eye by replacing the misshapen cornea with the front curve of a contact lens which is calculated to render the eye emmetropic (a state where no visual correction is necessary). When the lens is taken off, however, the cornea is still misshapen or defective and refractive errors still exist.

The cornea is very pliable and can be reshaped with a series of progressive contact lens changes. This procedure is known as Orthokeratology. The methods of Orthokeratology without the use of enzymes or other agents originated in 1962 as an extension of normal contact lens use. Orthokeratology is generally defined as the therapeutic use of contact lenses to reshape the corneal curvature, thereby improving refractive errors of the eye. Dr. Charles May and Dr. Stuart Grant are credited with pioneering the process. University and clinical level research over the next 20 years confirmed the safety, effectiveness, and retention of this procedure. Orthokeratology has today become a contact lens specialty practice for a limited number of private practitioners primarily in the United States.

The traditional Orthokeratology procedures use a series of progressive contact lens changes to reshape the cornea, producing less curvature and a more spherical shape. This reduces or eliminates myopia and astigmatism and improves natural vision. Retainer contact lenses are then worn to stabilize the results. The contact lenses are rigid gas permeable material with no enzyme/agents. The program length varies from six to eighteen months with progressive contact lens changes and examinations each two to six weeks.

A common fitting formula for Orthokeratology is as follows:

Lens Base Curve In Diopters = Flattest central corneal curvature in diopters to 1.0 diopter flatter.

Lens Diameter = Base curve in mm + 1.5 mm $$\text{Power} = \text{Subjective } Rx \pm \frac{\text{Base Curve}}{\text{Central Curvature}} \text{ relationship}$$

Thickness = .18 mm for 0 power — subtract .01 mm for each 1 diopter minus; add .02 mm for each 1 diopter of plus Intermediate Curve = Base Curve in mm + 1.5 mm, width = .35 — .5 mm Peripheral Curve = Base Curve in mm + 3.0 mm, width = .35 — .5 mm As the Orthokeratology program progresses, for myopia new contact lenses are refit with flatter curvatures, less correction, larger diameters, and greater thickness. The patient's central corneal curvature continues to lessen (flatten and become more spherical), myopia and astigmia are reduced, and unaided (natural) visual acuity improves significantly. When maximum desired results are achieved or the patient ceases to improve, retainer contact lenses are worn full time or part time to stabilize results.

For traditional Orthokeratology procedures, university and clinical research indicates the following limits of change: 4 diopters of myopia and 2.5 diopters of astigmatism change, no appreciable hyperopia change, 2 diopters of central corneal change, and 9 lines of unaided visual acuity change on the Snellen chart. Regression may occur in hours or days if retainer lenses are not worn.

Notwithstanding the foregoing, there remains a need for an improved method of correcting refractive errors in the eye nonsurgically which can correct larger amounts of refractive errors, produce relatively permanent results, in a much shorter period of time.

SUMMARY OF THE INVENTION

There has been provided in accordance with one aspect of the present invention a method of correcting refractive errors of the eye. The method comprises the steps of administering a corneal softening amount of an agent that temporarily softens the cornea so that it can be reshaped from a first configuration to a desired second configuration. Typically, the desired second configuration will produce emmetropia (no refractive error).

The cornea is thereafter fitted with a rigid contact lens having a concave (posterior) shape of the desired second configuration so that the convex (anterior) cornea will reshape (mold) from the first configuration to the second rendering the eye emmetropic. The cornea is thereafter permitted to reshape to the desired second configuration under the influence of the lens. Preferably, after the cornea softening effect of the agent has substantially dissipated, the lens is removed.

In a preferred embodiment, the cornea softening agent comprises Hyaluronidase, together with pharmaceutically acceptable carriers and additives.

The cornea softening agent in accordance with the present invention is administered to the cornea in any of a variety of manners. Typically, the agent will be administered either directly in the form of eyedrops or via a cornea softening agent delivery vehicle which may comprise a contact lens. In one embodiment of the contact lens delivery vehicle, the cornea softening agent is impregnated into a collagen lens. The agent dissipates out of the lens into the cornea, and the lens preferably dissolves in the eye.

In accordance with a further delivery vehicle of the present invention, the cornea softening agent is stored in an annular chamber between the anterior and posterior surfaces of a rigid contact lens. A plurality of ports provide fluid communication between the cornea contacting surface of the lens and the chamber.

In accordance with a further embodiment of a delivery vehicle in accordance with the present invention, a rigid gas permeable contact lens center is provided with an annular soft contact lens flange extending radically outwardly all the way around the rigid center. The soft contact lens flange is impregnated with a cornea softening agent. The cornea softening agent is time released from the soft lens perimeter, and the rigid contact lens center reshapes the cornea to an emmetropic state.

In accordance with a further aspect of the present invention, there is provided a method of reshaping a cornea from a first configuration to a desired second configuration comprising the steps of first administering a cornea softening amount to temporarily soften the cornea. Thereafter, a first rigid contact lens is fitted to the cornea to reshape its anterior convex configuration to the desired concave (posterior) curvature of the first lens. Said first lens is thereafter removed and replaced by a second contact lens, having a second desired concave curvature. The convex cornea again reshapes to the new second lens concave configuration. A repeat process could be used for a third lens if necessary. The final lens will give the cornea a shape rendering the eye emmetropic.

These and additional features and advantages of the method and apparatus of the present invention will become apparent from the Detailed Description of Preferred Embodiments which follow, when considered together with the attached drawings and claims.

BRIEF DESCRIPTION OF THE DRAWINGS

FIG. 8B is a cross-sectional view taken along the lines 8b-8b in FIG. 8a.

DETAILED DESCRIPTION OF PREFERRED EMBODIMENTS

Figure 1:
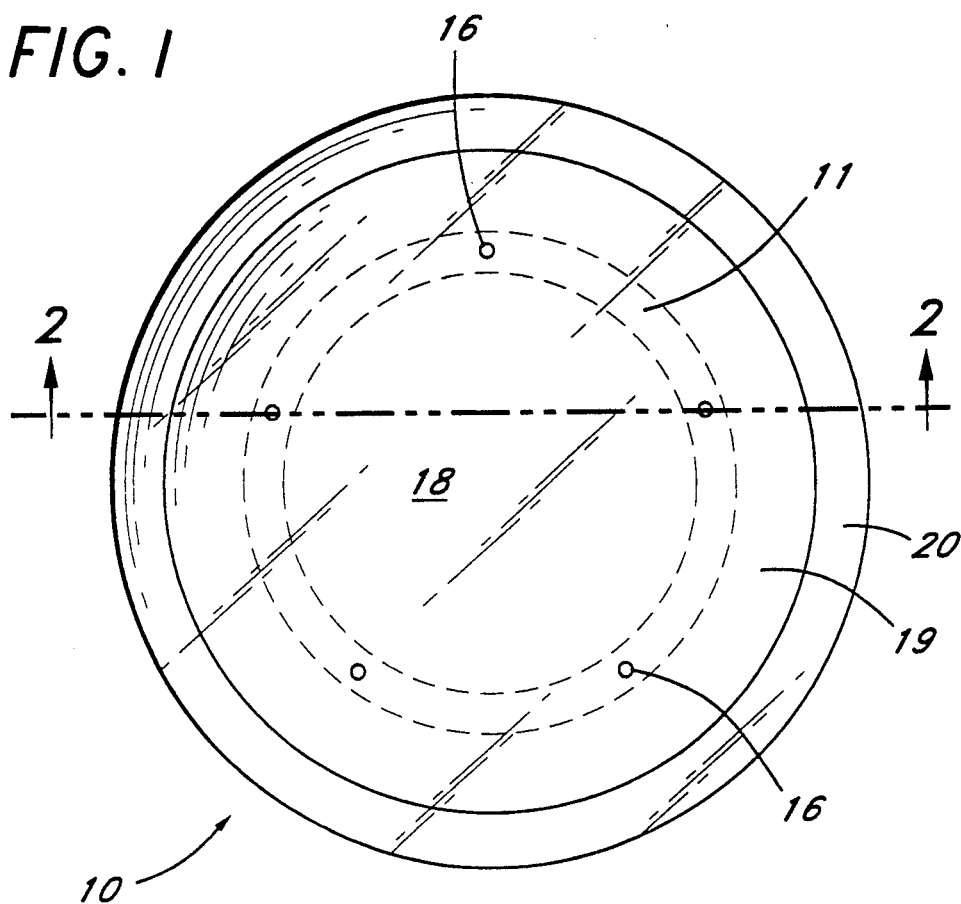
FIG. 1 is a plan view of an Enzyme-Orthokeratology rigid gas permeable contact lens for myopia.

In accordance with the method of the present invention, there has been provided an improved Orthokeratology method which the inventor refers to as Enzyme-Orthokeratology. Enzyme-Orthokeratology adds enzyme(s) and/or other agents to the Orthokeratology contact lens program. The enzymes and/or agents are time released into the cornea to soften it and make it more pliable, which enhances the corneal reshaping process. The reshaped cornea thereafter "hardens" to retain its new configuration.

Enzymes and Agents (Drugs and Chemicals) Used for Enzyme Orthokeratology

A number of enzymes may be used to perform Enzyme-Orthokeratology. A number of agents which include drugs and chemicals may also be needed. For simplicity, I will refer to these enzymes and other agents collectively as simply "enzyme."

Enzymes are protein molecules that speed up chemical reactions in animals and plants. The enzyme combines with the altered molecules to form a complex molecular structure in which the chemical reaction takes place. The unchanged enzyme then separates from the product(s) of the reaction. In a sense, the enzyme is a catalyst to speed up the chemical reaction.

In the preferred embodiment of the present invention, the primary enzyme used is Hyaluronidase. Hyaluronidase is a proteolytic enzyme that is a catalyst for the depolymerization of mucopolysaccharides. It breaks down the mucopolysaccharide chain. It also catalyzes the hydrolysis of the one to four linkages in hyaluronic acid, chondroitin and chondroitin 4 sulfates A & C. Mucopolysaccharide is the key intracellular ground substance (cement or glue) of the stroma, the connective type tissue of the middle layer of the cornea.

The shape of the cornea is based on the stromal collagen fibrils in parallel along with the mucopolysaccharide (cement or glue) layers between these fibrils. Hyaluronidase, which is specific to only the mucopolysaccharide layer, breaks down the mucopolysaccharide chain when released into the cornea chains. The stroma is therefore temporarily softened and the cornea becomes more pliable (moldable). In other connective tissue, Hyaluronidase enzyme decreases the viscosity of the intracellular matrix, promotes diffusion, and rapid spreading.

Hyaluronidase may be obtained from any of a variety of sources, including bovine (bull) testes, ovine (sheep) testes, and Streptomyces (bacteria). The Hyaluronidase enzyme is preferably used as a lyophilized powder (freeze dried). One form of Hyaluronidase is available under the trade name Wydase ® available from Wyeth Laboratories, Inc., Philadelphia, Pa. The Wydase ® Hyaluronidase is a preparation of highly purified bovine testicular Hyaluronidase, and is available in two dosage forms. The lyophilized form is available as a sterile, white odorless amorphous solid powder and may be reconstituted with sodium chloride injection USP before use, typically in the proportions of about 1 milliliter per 150 USP units of Hyaluronidase. A Hyaluronidase solution is also available, containing 150 USP units of Hyaluronidase per ml, with 8.5 mg chloride, monobasic sodium phosphate buffer, and no more than about 0.1 mg thimerosal.

In the preferred embodiment, the lyophilized form of the enzyme is preferably placed in a solution comprising sodium phosphate as a buffer to keep the pH proper, sodium chloride, distilled H$_2$O to dissolve the enzyme, bovine or human albumin to preserve the effectiveness and activity of the enzyme, and other agents such as HCl and sodium hydroxide to adjust the pH up or down. Other drugs such as proparacaine hydrochloride may be included to anesthetize the cornea as well as to soften it slightly. Dychloride, hydrochloride, dicthylominoacet-2, oxylidide hydrochloride and chlorine also may assist in the softening process. Other enzymes or formulations may also provide acceptable results, as can be readily determined through routine experimentation by one of skill in the art in view of the present disclosure.

The optimum enzyme concentration will vary depending upon the length of the overall protocol, nature of the drug delivery vehicle and possibly the degree of change in shape desired in a given patient. In general, concentrations within the range of from about 50 units/ml to about 300 units/ml, preferably within the range of from about 100 units/ml to about 200 units/ml, and most preferably about 150±10% units/ml are used.

A sample enzyme formula to produce a formulation having about 150 units/ml would be as follows: 15,000 units of bovine Hyaluronidase enzyme (lyophilized powder form) is combined with 100 ml distilled H$_2$O and 0.7 grams NaCl. This is added 0.14 grams NaPO$_2$ Dibasic (0.01 molar) and 0.1 gram bovine serum albumin. The pH is tested and maintained at a level of 5-7 (near the biological pH). HCl (0.05 molar) drops can be added to lower the pH and NaOH added to increase the pH.

The above Hyaluronidase enzyme formula may then be added to a chamber inside the rigid gas permeable lens as shown, or soaked into the special soft lens as shown or combination of soft and rigid lens as shown. Typically, dosage volumes in the range of from about 2 drops to about 6 drops, and preferably between about 3 drops and 5 drops of 150 units/ml formulation will be used. Dosages for different refractive conditions and delivery vehicles can be optimized through routine experimentation by one of skill in the art. The lenses are then placed on the cornea to release the enzyme formula into the cornea. The enzyme formula may also be injected directly into the cornea or used in drop form.

Methods of Releasing Enzyme/Agents Into the Cornea

In accordance with a first method of the present invention, rigid gas permeable contact lenses 10 (FIGS. 1-2) are made from known fluoro silicone acrylate lens material. The lens is provided with an internal chamber 11 for storing the cornea softening agent. The chamber 11 preferably comprises a radially symmetrical space encircling the entire lens 10 between the anterior surface 12 and posterior surface 13 of the lens 10.

Rigid lenses for the present purpose can conveniently be made by lathe cutting, molding, or milling a posterior component and an anterior component from a contact lens button which, during fabrication, can be secured together to form a unitary lens using bonding techniques or adhesives known in the art. The chamber 11 is preferably formed by lathe cutting an annular recess into the convex surface of the posterior component of the lens before the final lens fabrication. Although any of a variety of dimensions can be used in accordance with the present invention, a preferred lens 10 is provided with an annular chamber 11 having a width of approximately 1.0 mm to about 1.5 mm and a depth of from about 0.05 mm to about 0.10 mm.

A plurality of microscopic holes 16 are provided in the posterior portion of the lens 10 to allow fluid communication between chamber 11 and the eye, thereby facilitating the timed release of the enzyme/agents into the cornea. These holes 16 may be provided by mechanical or laser drilling, or by molding prior to assembling the anterior component and posterior component of the lens. Preferably, holes 16 are drilled using a mechanical drill having a microcarbon drill bit.

The pumping action of the eyelids combined with natural tearing assists the timed release of the enzyme/agents through the tiny holes 16. Preferably, the holes produced by mechanical drilling with a microcarbon bit will have a diameter of from about 0.002 mm to about 0.010 mm, and preferably about 0.005 mm. The number and diameter of holes 16 can be varied to affect the time release characteristics, as will be apparent to one of skill in the art. In general, however, for the diameter ranges specified above, from about 3 to about 10 holes are contemplated to be used.

Figure 2:
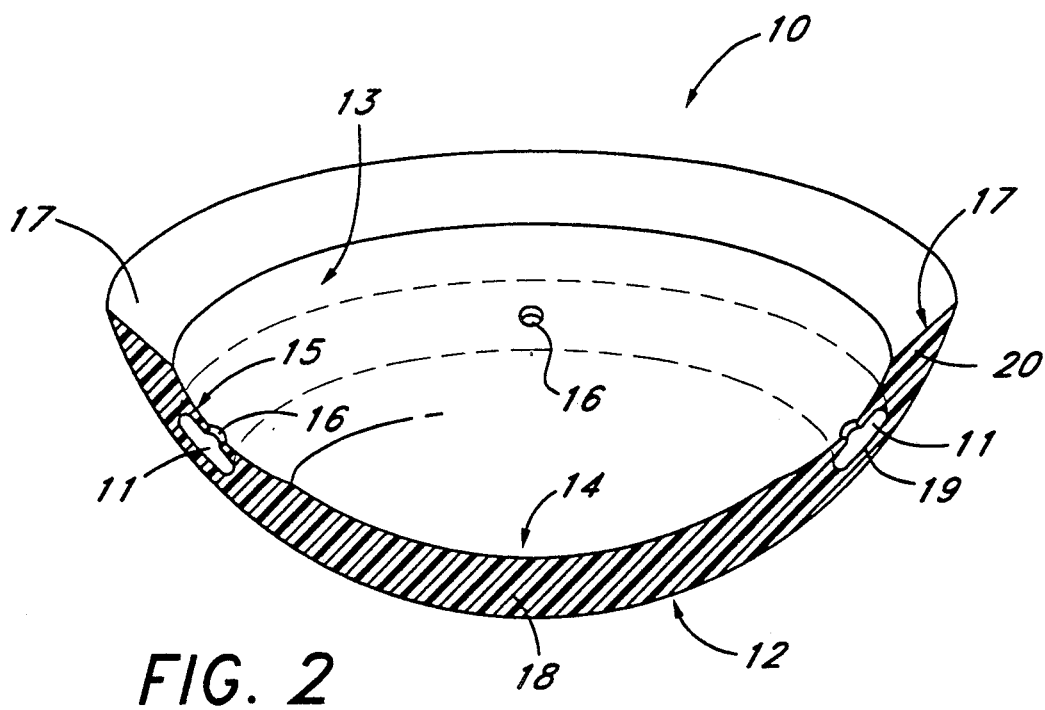
FIG. 2 is a cross-sectional view taken along the lines 2—2 on FIG. 1.

In a preferred embodiment of the lens 10 of FIGS. 1 and 2, the posterior portion of the lens has a centerpoint thickness of approximately 0.12 mm and an annular recess is lathed to a depth of about 0.075 mm. Five holes 16, each having a diameter of about 0.005 mm, are drilled through the bottom of chamber 11 and spaced equidistantly apart around the periphery of the chamber 11 to provide communication with the posterior surface 13 of the lens.

The anterior portion of the lens, having a centerpoint thickness of about 0.12 mm is thereafter secured to the posterior portion to enclose the annular recess and form chamber 11, thereby forming a lens having an overall center thickness of about 0.24 mm. Bonding is accomplished by dabbing a small amount of an instant glue such as Super Bonding ™ glue for contact lenses apparent to one skilled in the art.

Posterior radii of curvature (Base curve 14, intermediate curve 15 and peripheral curve 17) of the lens 10 are selected that will reshape the anterior corneal curvature to a shape required for rendering the eye emmetropic (no correction). The posterior and anterior configurations of the contact lens in accordance with the present invention are similar to those used in conventional Orthokeratology fitting procedures. In general, the convex anterior surface of the lens 12 approximates a substantially uniform radius of curvature along all planes (i.e., approximating a portion of the surface of a sphere). The concave posterior surface 13 of the lens 10 is divided into several discrete zones, each having a unique curvature. For example, referring to FIG. 2, a posterior central base curve 14 is radially symmetrically disposed about the centerpoint of the lens 10. An intermediate posterior curvature 15 is disposed annularly about the radial outer periphery of the posterior central base curve 14. Adjacent to the radially outward side of the intermediate posterior curvature 15 is a third peripheral posterior curvature 17. Thus, the lens 10 can be considered to comprise three distinct zones shown in FIG. 1, a central optic zone 18, an intermediate zone 19, and a peripheral zone 20. Preferably, in accordance with the present invention, an annular chamber 11 is disposed within the intermediate zone 19.

Day and/or night wear of these Enzyme-Orthokeratology lenses may be used. The cornea can be softened and reshaped in a matter of hours to a few days, and reshaping progress can be monitored using conventional methods. See rigid contact lens design section, infra, for lens parameters.

Figure 3A:
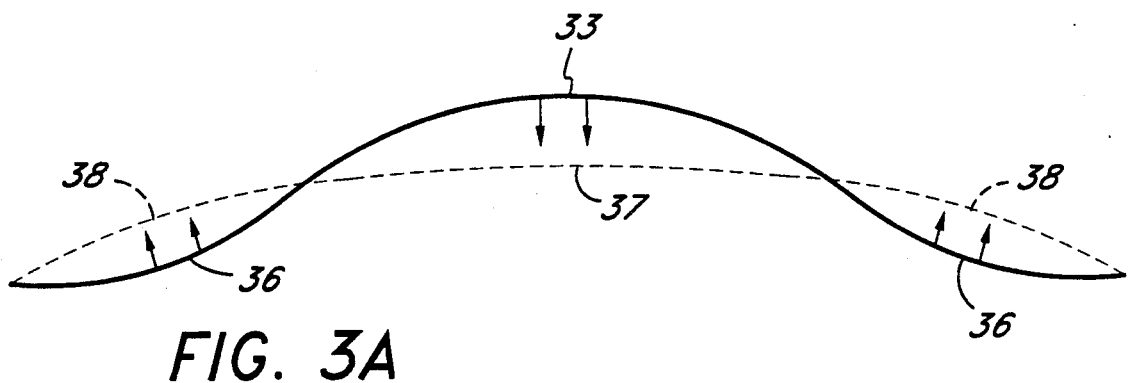
FIG. 3A is a schematic representation of the cross-sectional configuration of a myopic cornea, in solid lines, compared to the ideal shape shown in phantom, following the method of the present invention.

The lens 10 of the present invention can be utilized to correct myopia (FIG. 3A), astigmatism (FIGS. 4A-D), hyperopia as detailed infra. Hyperopia can be corrected (FIGS. 5A-B) with lens designs (FIGS. 5C-D)

Figure 6:
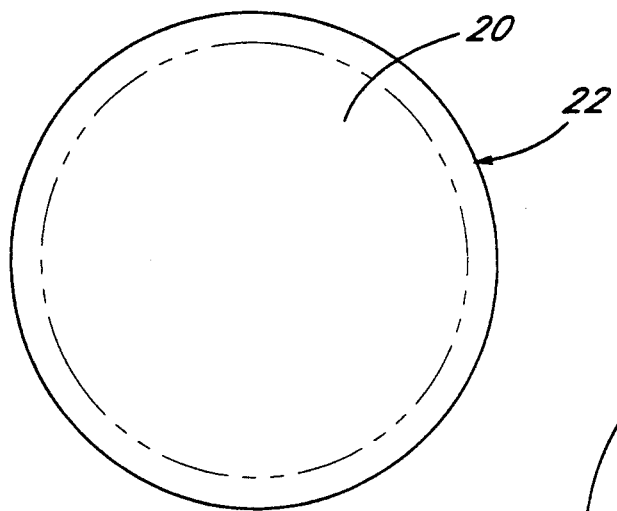
FIG. 6 is a plan view of an enzyme releasing soft collagen contact lens.

In accordance with a further delivery method of the present invention, a soft lens bandage or shield 22 (FIG. 6) is soaked or charged with a unit dosage of the enzyme/agents. The soft lens is then properly fit to the cornea and worn for a matter of hours to time release the enzyme/agents into the cornea. After the enzyme/agents sufficiently soften the corneal stroma, the soft lens either dissolves or is taken off.

One type of soft lens for use with this method is a collagen material which tends to uptake a relatively high volume of enzyme/agents and time release them relatively slowly. The material may be highly purified bovine collagen. The diameter preferably ranges from about 13.5 mm to about 16 mm. Base curves preferably range from about 8.0 mm to about 9.5 mm. The DK should be about 50 and the $H_2O$ hydration % should be about 83%.

One lens which has been found to be particularly well suited for the practice of this aspect of the present invention is the Medilens TM corneal shield available from Chiron Opthalmics, Inc. of Irvine, Calif. The Medilens TM corneal shield is a clear, pliable thin film fabricated from bovine tissue. This tissue has a high percentage of collagen closely resembling the collagen molecules of the human eye.

The Medilens TM corneal shield is stated to provide protection and lubrication to the ocular surface, gradually dissolving within approximately 24 hours. The dry weight of the lens is approximately 5.5 mg, and wet weight following loading with the enzyme of the present invention is approximately 34 mg. Loading is accomplished by soaking the lens in a solution, as previously described, for approximately 60 minutes at room temperature. The uptake of the lens has been measured to be approximately 28.5 mg, and the hydration of the lens is approximately 84%. In volume terms, the uptake of the lens is approximately 200-300 $\mu l$ (microliter). This is equivalent to approximately 4-6 drops of solution or 28 mg at a 150 unit/ml concentration.

Another type of soft lens material tends to uptake less enzyme/agents and release it more quickly. Common hydrophilic soft lens materials such as etafilcon A and phemfilcon A, available from Vistacon and Wesley Jessen, may be used with similar parameters as the collagen lens. These lenses can be the disposable or long-term wear variety. The $H_2O$ content should be about 58%.

After the soft lens 22 or other delivery vehicle has released the enzyme/agents into the cornea and softened it (made it more pliable), a rigid gas permeable contact lens with no enzyme is then fit to the cornea. The rigid contact lens rapidly reshapes the softened cornea. A contact lens posterior radius is used that will reshape the anterior cornea to a curvature required for emmetropia. The reshaping process may take from a few hours up to a few days. See rigid contact lens parameters section, infra.

In accordance with a further embodiment of the present invention, a saturn-type contact lens 24 (FIG. 7) is utilized. This type of lens comprises a lens with a rigid gas permeable center 26 and a soft lens peripheral skirt 28. The rigid gas permeable center 26 contains no enzyme/agents whereas the soft lens peripheral skirt 28 is soaked in the enzyme/agents.

Figure 7:
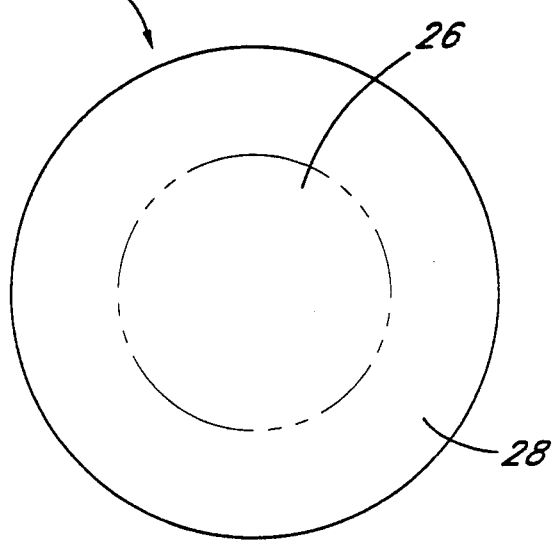
FIG. 7 is a plan view of a saturn-type enzyme releasing lens.

The peripheral skirt 28 of the saturn-type lens 24 may be manufactured from synergicon. A copolymer available from Precision-Cosmet. The rigid non-hydrophilic center 26 is typically from about 5.5 mm to 6.5 mm in diameter and has only about 0.2% $H_2O$ absorption (FIG. 7). The outer periphery 28 is polymerized into a soft hydrophilic skirt extending circumferentially about the outer periphery of the center 26 and has a width of from about 3.0 to 4.0 mm, and about 25% $H_2O$ absorption. The base curve of this saturn lens is from 7.2 mm to 8.2 mm.

As the saturn-type lens 24 is worn, the enzyme/agents are released into the cornea from the soft peripheral skirt 28, softening the cornea in hours. The rigid center of the saturn lens 26 immediately begins reshaping the softened cornea. The rigid center 26 has a posterior radius of curvature that will reshape the anterior cornea to a curvature required for emmetropia as has been discussed. The cornea is reshaped from hours to a few days. The soft lens skirt 28 gives added comfort and less edge sensation which helps the Orthokeratology process and encourages retainer lens wear.

The enzyme/agents dissipate out of the cornea in a few days and the cornea hardens to its new shape. The saturn lens 24 or another rigid retainer is preferably worn for a few more days to stabilize the new corneal shape. The lens is then removed.

Delivery of the corneal softening agent may be accomplished in any of a variety of additional ways known in the art for other ocular medications. For example, eye drops of enzyme/agents may be directly applied to the central cornea. Needle injection of the enzyme/agents directly into the cornea is also a possibility. A rigid gas permeable lens is then immediately fit to the cornea to hold most of the drops on the cornea and to reshape the cornea. This contact lens is typically larger than usual prescription lenses and has different peripheral curves to hold the drops in place. As the cornea is softened, the rigid contact lens immediately begins reshaping the cornea to a shape which renders emmetropia.

Figure 8A:
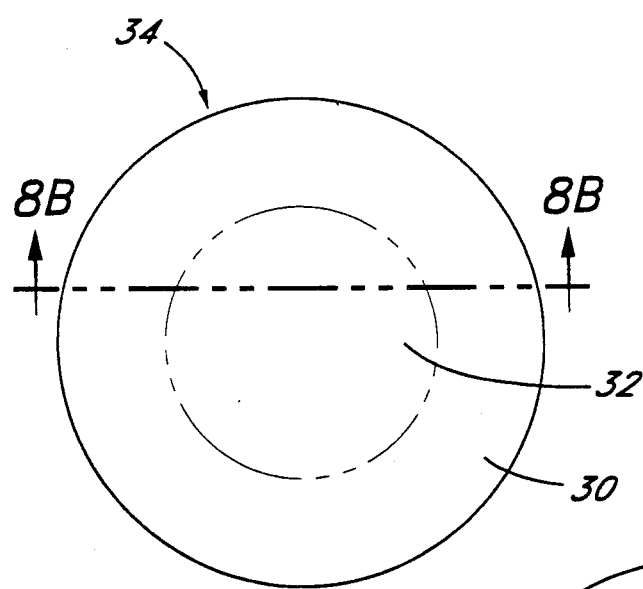
FIG. 8A is a plan view of a "piggy back" enzyme releasing Orthokeratology lens.
Figure 8B:
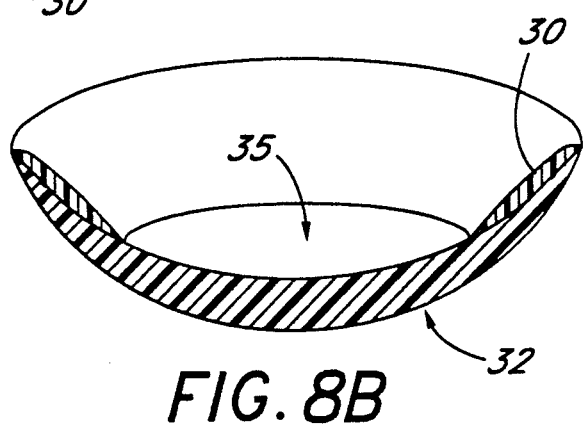
Figure 9:
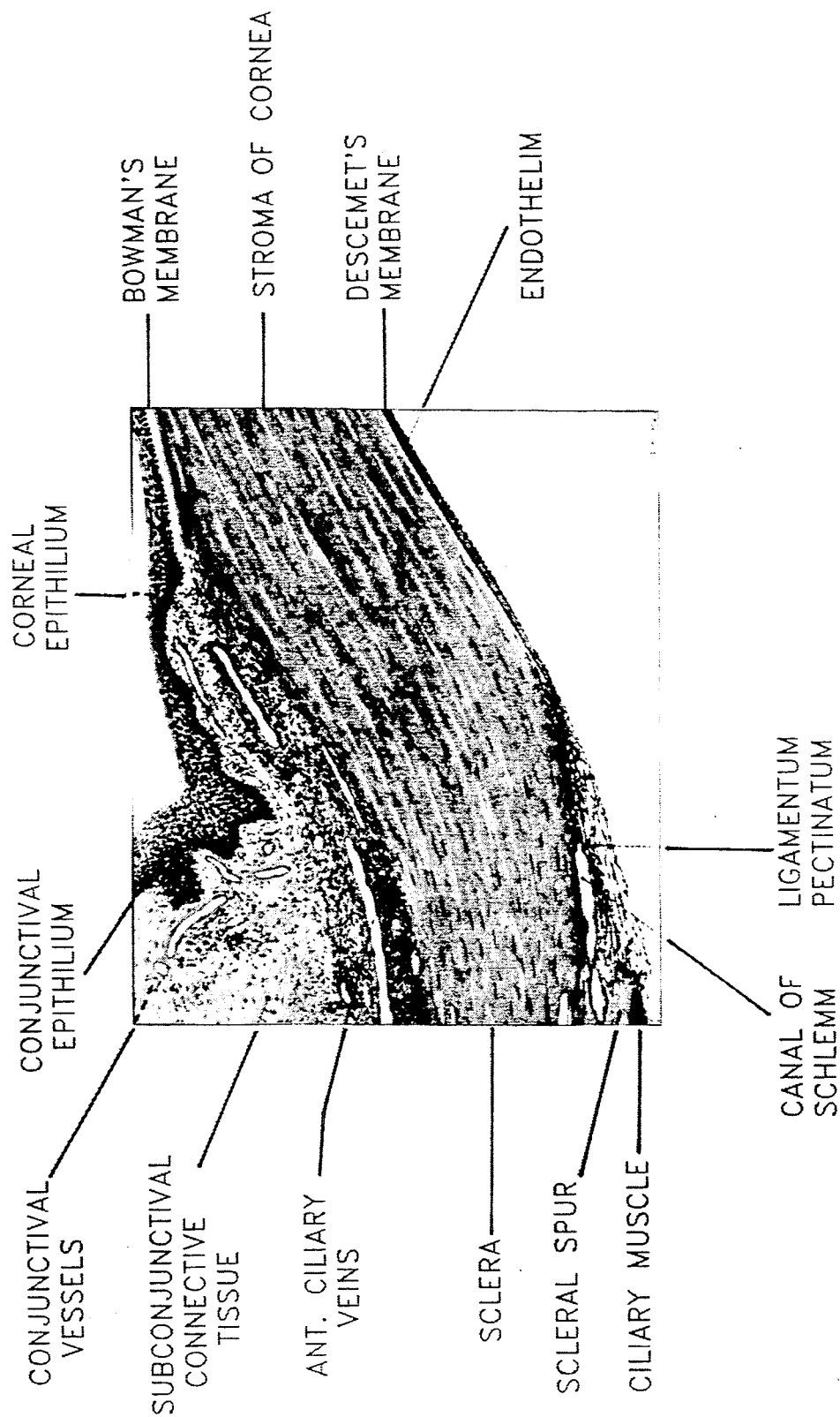
FIG. 9 is a microphotograph of a cross section of the human cornea.
Figure 10:
FIG. 10 is an enlargement of the microphotograph illustrating the human stroma (collagen fibrils and mucopolysaccharide layers).

A "piggy back" contact lens system 34 (FIGS. 8A and 8B) may also be used to release the enzyme/agents into the cornea and simultaneously reshape it. In this embodiment of the present invention, an annular ring 30 of soft lens type material is fused to the inside intermediate curve and peripheral curve of a rigid gas permeable contact lens 32. The resulting piggy back (soft) lens 34 is soaked in the enzyme/agents, and the enzyme is retained in the soft lens portion 30. The enzyme is then time released into the cornea, which softens it.

The rigid gas permeable center 32 has a posterior central curvature 35 that reshapes the anterior cornea's curvature to a shape rendering the eye emmetropic. The rigid gas permeable contact lens center 35 is preferably a fluoro-silicone-acrylate material. The Dk is 60-92. The diameters vary from about 7.5 mm to 10.5 mm and the base curves 35 of the rigid lens 32 vary from about 7.0 mm to 9.0 mm. The "fused on" soft lens portion 30 is a hydrophilic soft lens material such as etafilcon A or phemfilcon A. Attachment of the annular ring 30 to the rigid contact lens 32 is accomplished by an adhesion process. The width of soft annular ring 30 varies between about 0.75 and 1.5 mm each side.

The Enzyme-Orthokeratology Procedure

The Enzyme-Orthokeratology contact lens must be properly fit to the anterior surface of the cornea. The enzyme/agents are then time released and secreted through the corneal epithelium and Bowman's membrane, finally reaching the stroma (substantia propria). The enzyme is effective only at this stromal layer.

The corneal stroma is made up of collagen fibrils in parallel which are about 1/10 of a wavelength apart. This maintains the transparency of the cornea. Mucopolysaccharide, "a cement or glue type substance," lies between the collagen fibrils to form the corneal shape.

The Hyaluronidase enzyme is specific only to the mucopolysaccharide chain. It will soften, breakdown or depolymerize the mucopolysaccharide chain. The "glue or cement" of the stroma is softened and the cornea becomes temporarily more pliable. The corneal reshaping process causes the collagen fibrils of the stroma to shift, rearrange slide, and change length to form a new shape while the cornea maintains good integrity and transparency. The anterior cornea then rapidly reshapes to the inner curvature of a rigid gas permeable contact lens with the proper shape to create emmetropia (no refractive error).

Figure 3B:
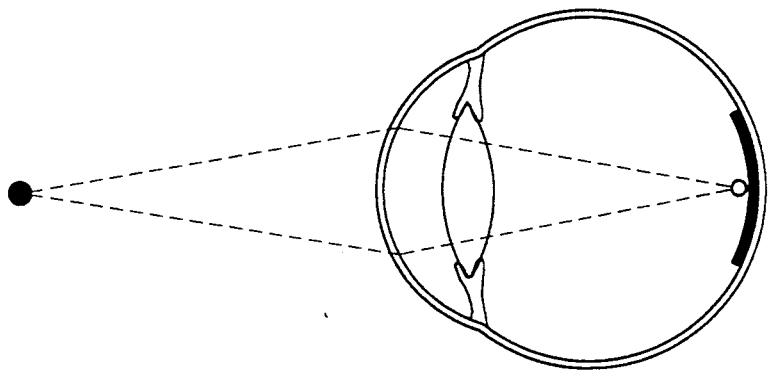
FIG. 3B is a schematic illustration of the convergence of light on the retina in an eye having normal vision.
Figure 3C:
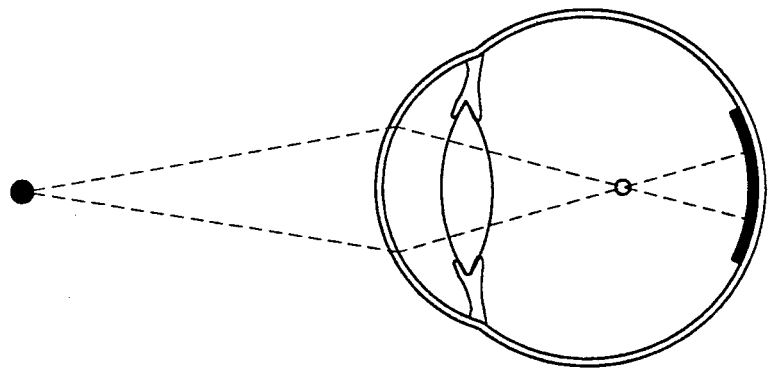
FIG. 3C is a schematic representation of the convergence of light in front of the retina in a nearsighted (myopic) eye.

In the case of myopia (FIG. 3A), the cornea usually begins with a positive shape, steeper in the center 33, flatter in the periphery 36. After the rigid gas permeable lens is placed on the eye, the force of the eyelids and lens movement cause flattening of the central corneal curvature 37. The internal pressure of the eye causes the paracentral cornea 38 to move outward or steepen. The cornea becomes spherical with a more minus shape and less central curvature (37, 38). The light entering the cornea is therefore refracted less, that is, further back towards the retina (FIG. 3B). This then reduces or eliminates myopia, which causes light to be refracted more and thus causes images to be focused in front of the cornea (FIG. 3C).

Once the proper corneal shape is achieved, the enzyme/agents dissipate out of the cornea and the cornea hardens. A retainer contact lens (not illustrated) is worn for a short period of time (a few days) to stabilize the cornea. It is then removed. The retainer lens has the same rigid gas permeable contact lens parameters as mentioned in FIGS. 1 and 2. The lens has no enzyme and is the final lens of enzyme Orthokeratology treatment. Its posterior curvature retains the new corneal shape creating emmetropia. The new mucopolysaccharide chain (cement or glue) and the new collagen fibril alignment conform to the new shape imposed on them by the rigid lens. They retain this shape with a new memory of only the new shape. Stability and permanency is maintained without a retainer lens.

Contact lenses or spectacles will not be required for good visual acuity after the Enzyme-Orthokeratology lenses are removed. With previous Orthokeratology methods using no enzymes, if the retainer contact lenses were removed, the cornea would tend to regress back to its old shape, like a rubberband. This is because the unchanged mucopolysacchrides and collagen fibrils had a memory of only the old shape.

The metabolic processes of the cornea are greatly accelerated at higher temperatures. Reshaping will occur more quickly if the corneal metabolism is increased by applying heat. Heat radiation and other methods of heating the cornea could possibly be used along with Enzyme-Orthokeratology if desired. Heat is generally not necessary to reasonably rapidly reshape the cornea, however.

Rigid Gas Permeable Contact Lens Designs

One preferred embodiment of the rigid gas permeable contact lenses designed for Enzyme-Orthokeratology is described in the following paragraphs.

The lenses should be made of fluoro-silicone-acrylate material (methyl-methacrylate difluoroitaconate siloxanyl copolymer), available from Paragon Optical. The high oxygen permeability of this material DK60–DK92×10–11, allows sleeping in the lens if necessary. The lens has excellent wettability with a low wetting angle of 26. The base curve of the lens varies from 6.5 mm to 9.0 mm, depending upon the central corneal curvature. The total diameter of the lens is the base curve in mm +1.3 mm to 1.8 mm, and the range is 7.5 mm to 10.5 mm (total diameter FIG. 1).

The central optic zone 18 (FIG. 1) is transparent and corrects the refractive error of the eye soon to produce excellent visual acuity. The optic zone diameter ranges from 6.5 mm to 9.0 mm. The intermediate zone 19 contains the enzyme/agents chamber 11 to time release the enzyme formula into the cornea. The width of the intermediate zone 19 varies from 0.35 mm to 1.0 mm. The intermediate curve 15 may be steeper or flatter than the base curve 14 of the lens depending on the refractive error. The peripheral curve 17 is flatter than the base curve 14 of the lens. The width of the peripheral zone 20 varies from 0.35 mm to 1.0 mm. The peripheral curves 17 allow for tear circulation and oxygen exchange during blinking.

The power of the lens is based on the refractive error of the patient and the lens base curve to central corneal curvature relationship. The thickness is 0.20 mm for 0 power; 0.01 mm should be subtracted for each diopter of minus correction, and 0.02 mm should be added for each diopter of plus. The inner curvature of the optic zone (14 FIG. 2) (base curve) is calculated to make the eye emmetropic when the cornea is molded to this curvature. This may be accomplished with one to three lenses. The front curvature of the optic zone (12 FIG. 2) is of a radius calculated to give the subject no refractive error and 20/20 aided visual acuity while wearing the lens. The final lens will have zero refractive power. All of the rigid contact lens parameters vary depending upon the refractive error, corneal curvature and size, and fitting formula, as is known in the art. This lens design without enzyme may also be used to reshape the cornea after it has been softened with other enzyme releasing methods already mentioned.

Myopia Enzyme-Orthokeratology Procedure

For myopia, usually there is a positively shaped cornea (steeper in the center 33 and flatter paracentrally 36). See FIG. 3A. The base curve of the contact lens (14 FIG. 2) should usually be flatter than the central corneal curvature 33 up to the amount of the myopia in diopters. The inner radius of the intermediate zone 15 may be up to 4 diopters steeper than the base curve. The steeper central corneal curvature 33 is reshaped to a flatter curvature 37 and the flatter paracentral curvature 36 is reshaped to a steeper shape 38. The result is a spherical cornea from center to paracentral with a flatter central curvature. This eliminates myopia because the light is refracted further back on the retina (FIG. 3B) instead of in front of the retina (FIG. 3C), and there is less spherical aberration.

The following example illustrates the method for correcting myopia using Enzyme-Orthokeratology.

In this example, the patient exhibits 20/300 U.V.A. or 3 diopters myopia; a flattest central curvature of 45 diopters or 7.5 mm; and a paracentral curvature of 40 diopters and the cornea is positively shaped at +0.30. The initial enzyme formula taught by this invention in its hollow chamber 11. The base curve 14 is 42 diopters or 8.0 mm (3 diopters flatter than central curvature). The optic zone 18 width is 8.0 mm. The power of the lens is plano (0). The size of the lens is 9.6 mm (8.0+1.6 mm). Its thickness is 0.20 mm. The intermediate curve 15 radius is 7.5 mm or 45 diopters (3 diopters steeper than the base curve) with a width of 0.50 mm. The peripheral curve 17 has a radius of 10.0 mm, with a width of 0.30 mm.

The lens is loaded with a unit dose of Hyaluronidase enzyme formula (approximately 2 to 4 drops) of 150 units/ml by pressure injection through one of the holes 16 using a microscopic needle.

The contact lens is properly fitted to the cornea and the enzyme is time released into the cornea over the course of a few hours. The enzyme secretes through the epithelium and Bowman's membrane into the stroma where it softens the mucopolysaccharide layer. The softened pliable cornea reshapes its anterior central curvature (45 diopters) to the posterior base curve 14 of the lens (42 diopters). The cornea's new anterior central curvature becomes 42 diopters (3 diopters flatter than its original 45 diopters). The paracentral anterior cornea (40 diopters) steepens to 42 diopters=8.0 mm. The cornea now has a spherial shape. The original three diopters of myopia is now reduced to no correction (plano or emmetropic) and unaided (natural) visual acuity is improved to normal 20/20 from 20/300.

The enzyme dissipates out of the cornea over the following few hours to a few days and the cornea hardens with the new shape, rendering the eye emmetropic (no correction) and leaving normal, natural vision (20/20). The final enzyme orthokeratology lens is left on the eye for a few days after the cornea hardens to stabilize the corneal change and act as a retainer lens. It is then removed. New retainer contact lenses are fitted only if necessary to stabilize the new curvature over the period of a few more days, and the amount of time they must be worn everyday is reduced systematically until they are no longer worn at all. The new reformed cornea's memory system only knows the new shape so the cornea will not regress to its old shape in the absence of retainer lenses.

Astigmatism Enzyme-Orthokeratology Procedure

Figure 4A:
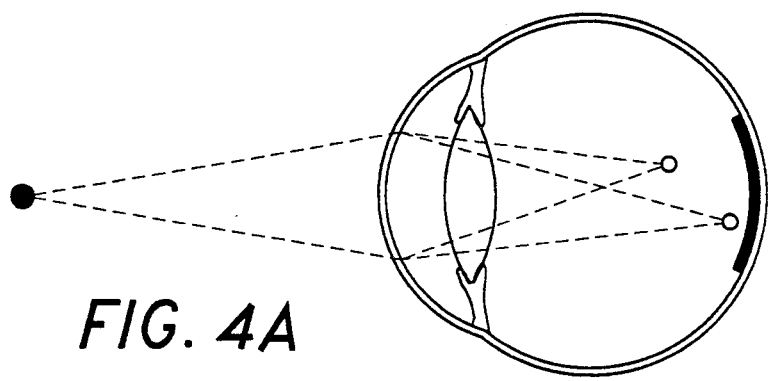
FIG. 4A is a schematic illustration of the convergence of light within the eye at more than one point, occurring in astigmatism.
Figure 4B:
FIG. 4B illustrates the central corneal curvature in an astigmatic eye, illustrating a shorter radius of curvature within a first plane and a relatively longer radius of curvature within a second plane substantially perpendicular to the first plane.
Figure 4C:
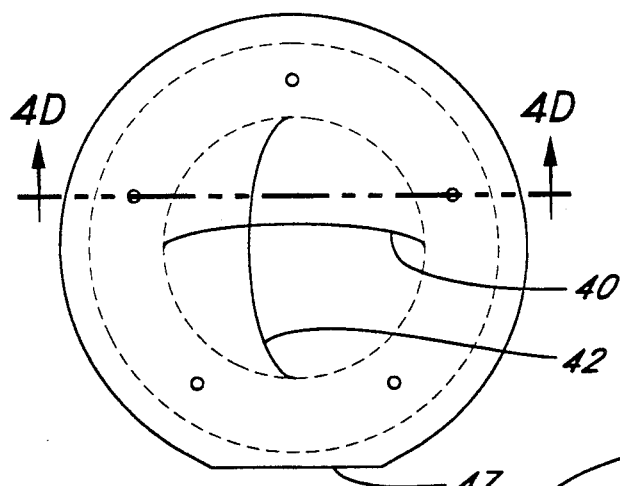
FIG. 4C is a plan view of a toric Enzyme-Orthokeratology contact lens for astigmatism.
Figure 4D:
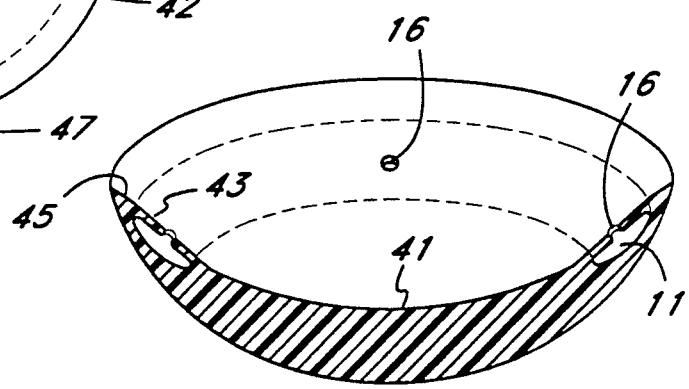
Figure 5A:
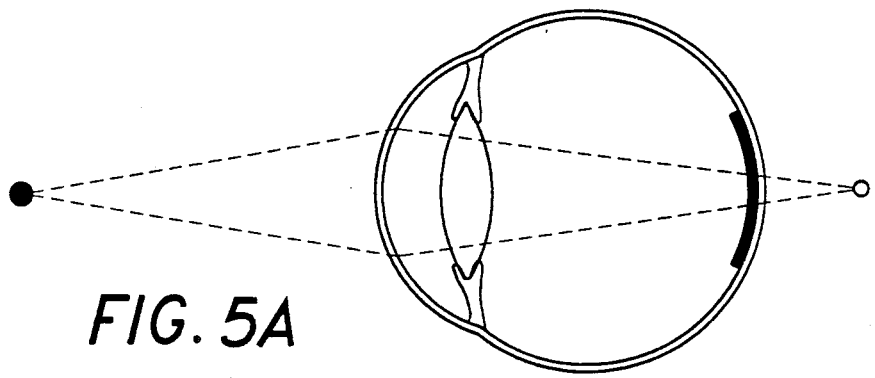
FIG. 5A illustrates the convergence of light behind the retina in the case of farsightedness (hyperopia).

For astigmatism, the central corneal curvature is uneven, which causes a stretching of the image on the retina (FIG. 4A). The horizontal and vertical central meridians are different curvatures (40, 42 FIG. 4B). The astigmatism contact lenses may use toric and aspheric base curves, 40, 42 FIG. 4C intermediate curves, and peripheral curves which may incorporate prism and/or truncation 47 FIG. 4C. The initially flatter central meridian of the eye 40 is reshaped to take on a steeper curvature 44 and the initial steeper central meridian 42 is reshaped to take on a flatter curvature 46. This process reshapes the central corneal curvature to a spherical shape and eliminates astigmatism.

To correct astigmatism using Enzyme-Orthokeratology, the following procedure may be used. In the preferred embodiment of the invention, the material for the lens is fluoro-silicon-acrylate. The base curves 41 (6.0 mm-8.5 mm) may be back toric, front toric, or bitoric. The flattest central corneal curvature is aligned with a steeper base curvature. The steeper central corneal curvature is aligned with a flatter base curvature. Aspheric base curves may also be used. The lens diameter is the base curve in mm+1.3 to 1.8 mm. The range is 7.5 mm to 10.5 mm. The optic zone 18 diameter equals the base curve in mm and ranges from 6.5 to 8.5 mm. The intermediate curve 43 radius ranges from 1 diopter to 2 diopters flatter than the base curve. The width is from 0.35 to 1.0 mm. The peripheral curves 45 range from 2 to 4 diopters flatter than the base curve 41. The width is 0.35 to 1.0 mm. The intermediate 43 and peripheral curves 45 may be aspheric. Prism and/or truncation 47 is used to keep the lens aligned in the proper position to reshape the astigmatic cornea.

The thickness of the lens varies with lens power. If zero lens power=0.20 mm, subtract 0.01 mm for each diopter of minus and add 0.02 mm for each diopter of plus power. The power of the lens is computed based on the patients refractive error and the base curve/corneal curvature relationship. The astigmatic lenses may incorporate the enzyme/agents in the chamber 11 as already discussed or be used without the enzyme after the cornea has been softened.

Hyperopia Enzyme Orthokeratology Procedure

Figure 5B:
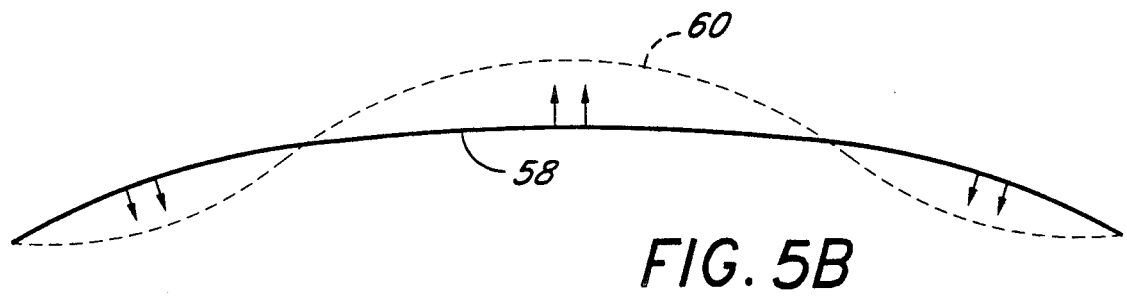
FIG. 5B illustrates the relatively flattened cornea before Enzyme-Orthokeratology in accordance with the present invention, in solid lines, and the shape of the cornea in phantom lines following the method of the present invention.
Figure 5C:
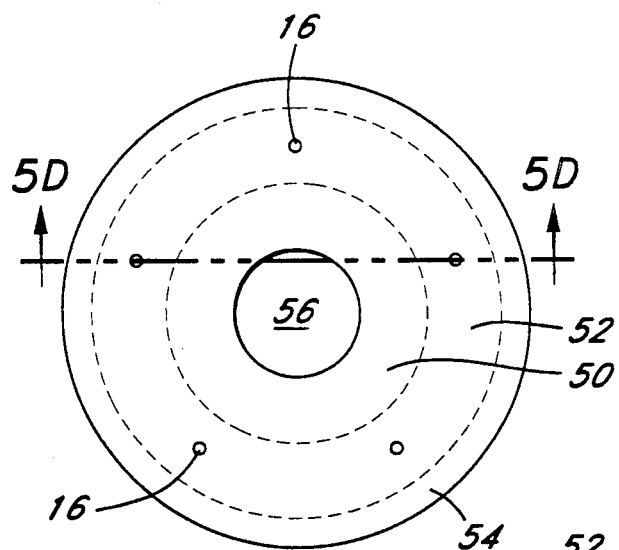
FIG. 5C is a plan view of an Enzyme-Orthokeratology contact lens for, hyperopia.
Figure 5D:
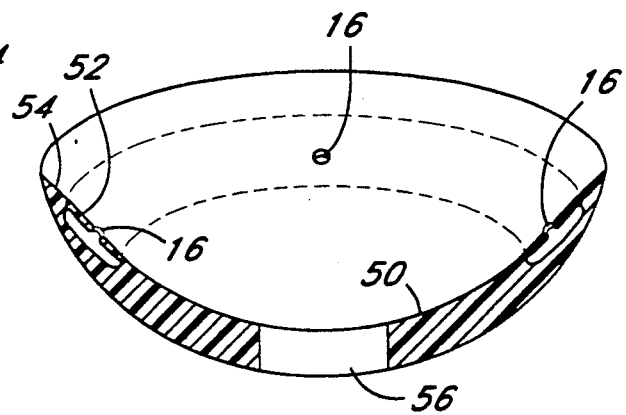
FIG. 5D is a cross-sectional view along the lines 5d-5d in FIG. 5c.

For hyperopia, the central curvature 58 of the cornea must be reshaped to a steeper curvature 60 (FIG. 5B). The light must be refracted more. The image, which is focusing behind the retina (FIG. 5A) needs to be moved forward onto the retina with more refraction, that is, more light bending at the cornea. The lens base curve (50 FIGS. 5C and 5D) may be fitted steeper than the central corneal curvature with flatter aspheric intermediate 52 and peripheral 54 curves. A hole 56 in the center of the lens may be used to encourage and give the space for the central cornea 51 to steepen.

To correct hyperopia using Enzyme-Orthokeratology, the following procedure may be used. In the preferred embodiment of the invention, a fluoro-silicone-acrylate material is used for the lens (FIG. 5C). A hole 56 ranging from 2.5 mm to 4.5 mm diameter is provided in the center. The base curve 50 of the lens is fit steeper than the central corneal curvature. The base curves 50 vary from 5.5 mm to 8.0 mm, and the diameter is the base curve 50 mm+1.0 mm to 1.5 mm (6.5 to 9.5 mm range). Smaller diameters are used because the curvature of lenses is steeper than that of the central cornea. The intermediate 52 and peripheral 54 curves should be aspheric curves 1.0 to 3 diopters flatter than the base curve 50. The width of these curves is 0.35 mm to 1.0 mm. The optic zone 50, 56 is between 5.5 mm to 8.0 mm. The thickness of the lens is dependent upon the power necessary for correction. With hyperopia the lenses will be thicker. If the power is plano (0) the thickness=0.20 mm, then add 0.02 for each diopter of plus. The power of the lens is computed based on the patients refractive error adjusted for the base curve/corneal curvature relationship. The hyperopic lenses may incorporate the enzyme/agents in the chamber 11 as already discussed or be used without the enzyme after the cornea is softened.

The drawings, parameters, constants, and concentrations set forth in this patent disclosure are given as examples and are in no way final, binding, or limiting. As many changes could be made in the above constructions and methods without departing from the scope of the invention, it is intended that all matter contained in the above description or shown in the accompanying drawings shall be interpreted as illustrative and not in a limiting sense.

I claim:

1. A method of correcting refractive error of the eye, comprising the steps of:
   administering a corneal softening amount of an agent that temporarily softens the mucopolysaccharide component of the cornea so that the cornea can be reshaped from a first configuration to a desired second configuration, wherein said agent comprises Hyaluronidase;
   fitting the convex cornea with a contact lens having a concave curvature of the desired second configuration;
   permitting the cornea to reshape to the desired second configuration under the influence of the lens; and
   thereafter removing said lens after dissipation of the corneal softening agent and stabilization of corneal curvature change.

2. A method as in claim 1, wherein said agent further comprises proparacaine hydrochloride.

3. A method as in claim 1, wherein said administration step comprises delivering said agent in eye drop form.

4. A method as in claim 1, wherein said administration step comprises delivering said agent from a contact lens having a reservoir of agent therein.

5. A method as in claim 1, wherein said administration step comprises fitting the cornea with a contact lens comprising a material which is impregnated with said agent.

6. A method of correcting refractive errors of the eye as in claim 5, wherein said material comprises collagen.

7. A method of correcting refractive error in the eye as in claim 1, wherein said lens is loaded with a unit dose of said agent, so that the agent is delivered to the cornea by the same lens which reforms the cornea from the first configuration to the desired second configuration.

8. A method of correcting refractive errors and making an eye emmetropic by accelerated reshaping of corneal tissue, comprising applying a rigid gas permeable contact lens that time release at least one agent into the cornea to soften the mucopolysaccharide component of the cornea and make the cornea more pliable, wherein the contact lens is preselected with a central concave radius equal to the convex radius required by the cornea to render the eye emmetropic, and wherein said agent comprises Hyaluronidase.

9. A method as in claim 8, wherein said Hyaluronidase is time released from a chamber lying between the anterior and posterior surfaces of the intermediate portion of the contact lens through a plurality of holes in the posterior surface for releasing said Hyaluronidase into the cornea to soften the mucopolysaccharide layer of the corneal stroma.

10. A method as in claim 8, wherein said agent further comprises proparacaine hydrochloride.

11. A method as in claim 8, wherein a series of rigid gas permeable contact lenses with time released agents are successively fitted with the cornea, wherein the central concave radius of each successive lens is progressively changed to produce emmetropia in the eye as the cornea radius of the cornea reshapes to the most recently installed contact lens radius.

12. A method as in claim 1, wherein the step of administering a corneal softening amount of Hyaluronidase includes injecting the Hyaluronidase directly into the cornea.

* * * * *